United States Patent
Aarts et al.

(10) Patent No.: US 6,706,856 B2
(45) Date of Patent: Mar. 16, 2004

(54) CRYSTALLINE MELAMINE AND ITS USE IN AMINO-FORMALDEHYDE RESINS

(75) Inventors: Veronika M. L. J. Aarts, Beek (NL); Tjay T. Tjioe, Sittard (NL); Koert Liekelema, Beek (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 10/136,447

(22) Filed: May 2, 2002

(65) Prior Publication Data

US 2003/0018158 A1 Jan. 23, 2003

Related U.S. Application Data

(63) Continuation of application No. PCT/NL00/00715, filed on Oct. 5, 2000.

(30) Foreign Application Priority Data

Nov. 2, 1999 (NL) .............................................. 1013456

(51) Int. Cl.[7] .............................................. C08G 73/06
(52) U.S. Cl. ........................ 528/424; 528/423; 528/422; 528/254
(58) Field of Search .................................. 528/424, 423, 528/422, 254

(56) References Cited

U.S. PATENT DOCUMENTS 4,565,867 A  1/1986  Thomas et al.

FOREIGN PATENT DOCUMENTS

| EP | 747366 | | 12/1996 |
|---|---|---|---|
| NL | 1006751 | | 4/1999 |
| WO | 9413664 | * | 6/1994 |
| WO | 96 23778 | | 8/1996 |
| WO | 98 55465 | | 12/1998 |
| WO | 99 46251 | | 9/1999 |

* cited by examiner

Primary Examiner—Duc Truong
(74) Attorney, Agent, or Firm—Pillsbury Winthrop LLP

(57) ABSTRACT

Multicrystalline melamine powder having a specific area of from 0.7-5 $m^2/g$, content of oxygen-containing components of less than 0.7 wt %, an APHA colour less than 17 and a melam content higher than 1.5 wt %. The multicrystalline melamine powder may be used in amino-formaldehyde resins.

12 Claims, No Drawings

CRYSTALLINE MELAMINE AND ITS USE IN AMINO-FORMALDEHYDE RESINS

This application is a continuation of PCT/WL 00/00715 filed Oct. 5, 2000.

The invention relates to crystalline melamine, more in particular to multicrystalline melamine powder and its use in amino-formaldehyde resins.

Melamine is prepared in various ways on an industrial scale. There are methods involving the crystallisation of melamine from an aqueous solution, there is a process in which melamine is obtained directly from a gaseous phase, and there is a method in which melamine is synthesised at a high pressure (7–25 MPa) and in which the melamine melt thus obtained is sprayed in an ammonia atmosphere and cooled. This last method yields a crystalline powder that may be used as such without further purification steps.

Crystalline melamine obtained according to the first method consists of a very pure melamine, but the crystals are relatively large, so that the dissolution rate in a solvent such as, for instance, water or a water/formaldehyde mixture is low. The melamine thus obtained is often ground to obtain more suitable smaller particles. While smaller particles do have a higher dissolution rate, they also have a lower bulk density and often poorer flow properties. As a result, the product obtained is not optimal in terms of the combination of dissolution rate, bulk density and flow properties. Melamine recovered directly from the gas phase is very fine and consequently has a poor bulk density and often poor flow properties. Crystalline melamine obtained according to the method involving spraying and cooling of a melamine melt in an ammonia atmosphere is a multi-crystalline melamine powder having good dissolution and reactivity properties in combination with reasonable flow properties.

Multicrystalline melamine powder consists of multicrystalline particles. This means that the larger particles (>20 $\mu$m) are composed of a multiplicity of small crystals, bonded together to form large porous particles. As a result, multicrystalline particles have both a high specific surface area normally associated with small particles while at the same time having advantages of larger crystals such as good flow properties. Scanning Electron Microscope pictures show a clear distinction between these particles and melamine crystallised from water. The particles obtained by spraying a melamine melt in an ammonia atmosphere have a cauliflower-like structure. The melamine crystallised from water contains a substantial amount of crystals having a crystal size greater than 50 $\mu$m.

A method for the preparation of multicrystalline melamine at high pressure in which a melamine melt is obtained that is cooled in an ammonia atmosphere is described inter alia in U.S. Pat. No. 4,565,867. In particular, this patent specification describes how urea is pyrolysed in a reactor at a pressure of from 10.3 to 17.8 MPa and a temperature of from 354 to 427° C. to produce a reactor product. This reactor product contains liquid melamine, $CO_2$ and $NH_3$ and is transferred as a mixed stream under pressure to a separator. In this separator, which is kept at virtually the same pressure and temperature as the said reactor, the said reactor product is separated into a gaseous stream and a liquid stream. The gaseous stream contains $CO_2$ and $NH_3$ off-gases and also melamine vapour. The liquid stream mainly comprises liquid melamine. The gaseous stream is transferred to a scrubber unit, while the liquid melamine is transferred to a product-cooling unit. In the scrubber unit, the said $CO_2$ and $NH_3$ off-gases, which contain melamine vapour, are scrubbed, at virtually the same pressure as the pressure of the reactor, with the molten urea needed for the process in order to preheat the urea and to remove the melamine present from the waste gases. Then the preheated molten urea, which contains the said melamine, is fed to the reactor. In the product cooler the liquid melamine is reduced in pressure and cooled with a liquid cooling medium to produce a solid melamine product without scrubbing or further purification. U.S. Pat. No. 4,565,867 preferentially uses liquid ammonia as the liquid cooling medium.

A drawback of the method according to U.S. Pat. No. 4,565,867 is that the melamine obtained has a yellowish color, as a result of which it cannot be used in all melamine applications.

Multicrystalline melamine obtained according to U.S. Pat. No. 4,565,867 can be used in amino-formaldehyde resins in which the color of the melamine is of minor importance. Amino-formaldehyde resins, such as for instance melamine-formaldehyde resins (MF), urea-formaldehyde resins (UF) and melamine-urea-formaldehyde (MUF) resins are generally known. U.S. Pat. No. -A-5120821 describes a method for the preparation of melamine-formaldehyde resins starting from melamine that still contains 2–8% of the impurities of the melamine preparation process. These impurities comprise small amounts of for instance ammeline, ammelide, ureidomelamine, melem and melam. An increase in this combination of impurities is unfavourable in particular for use in amino-formaldehyde resins for transparent applications. A too high content of oxygen-containing compounds for instance reduces the pH of the resin solution and this may result in unstable resins. The pH reduction is caused by, inter alia, the oxygen-containing compounds ammeline, ammelide and cyanuric acid, ARCs for short (Ammeline-Related Compounds).

The object of the present invention is to obtain improved crystalline melamine powder by means of a high-pressure melamine process in which melamine is obtained as a dry powder directly from a melamine melt. More in particular the object of the present invention is to obtain crystalline melamine powder by means of a high-pressure melamine process with a high dissolution rate in water, acceptable flow properties, a low content of oxygen-containing compounds and a good color.

Surprisingly, it has been found that amino-formaldehyde resins with strongly improved properties can be obtained by using melamine, obtained by means of a high-pressure process, showing a combination of properties comprising a high melam content.

The invention relates to multicrystalline melamine powder, in particular multicrystalline melamine powder obtained by means of a liquid-phase process, with the following properties:

APHA color less than 17 more than 1.5 wt. % melam content of oxygen-containing components lower than 0.7 wt. % a specific surface area of between 0.7 and 5 $m^2/g$.

The melam concentration in the melamine powder is preferably greater than 2 wt. %, more in particular greater than 2.5 wt. %.

Preferably, the content of oxygen-containing compounds is lower than 0.4 wt. %. The ARC content among the oxygen-containing compounds is usually below 0.15 wt. %, preferably below 0.1 wt. % and in particular below 0.05 wt. %.

The specific surface area preferably lies between 0.9 and 3 $m^2/g$.

A customary method for determining the color of melamine is the so-called APHA colorimetry. This involves the preparation of a melamine-formaldehyde resin with an F/M ratio of 3, a formaldehyde solution being used which contains 35 wt. % formaldehyde, between 7.5 and 11.2 wt. % methanol and 0.028 wt. % acid (as formic acid). The theoretical solids content of the solution is 56 wt. %. 25 g Melamine is dissolved in 51 g of the above solution by rapidly heating the mixture to 85° C. After about 3 minutes all melamine has dissolved. 2 ml of a 2.0 mol/l sodium carbonate solution is added to this solution, which is followed by stirring for 1–2 minutes. After this, the mixture is rapidly cooled to 40° C. The color is determined by means of a Hitachi U100 spectrophotometer with a 4 cm glass cuvette by subjecting the above-mentioned solution to absorbance measurements at a wavelength of 380 nm and 640 nm with demineralised water as blank in the reference cuvette.

The APHA color is calculated using the following formula:

$$APHA = f*(A380 - A640)$$

where A380=absorbance at 380 nm;
A640=absorbance at 640 nm;
f=calibration factor.

The calibration factor f is determined on the basis of absorbance measurements at 380 nm on calibration solutions prepared from cobalt chloride and potassium hexachloroplatinate. A 500 APHA calibration solution contains 1.245 g potassium hexachloroplatinate (IV), 1.000 g cobalt (II) chloride and 100 ml 12 M hydrochloric acid solution per litre of calibration solution. With this calibration solution dilutions are made for calibrations at 10 and 20 APHA. The calibration factor f is calculated using the following formula:

$$f = APHA \text{ (calibration solution)}/A380$$

where APHA (calibration solution)=APHA value of the calibration solution and A380=absorbance at 380 nm.

The color of the multicrystalline melamine obtained with the method according to the invention is less than 17 APHA, preferably less than 15 APHA.

A customary method for determining the specific surface area is by means of gas adsorption according to the BET method. For a description of the BET method see S. Brunauer, P. H. Emmett, E. Teller; J.Am.Chem.Soc.; 60 (1938) 309.

Examples of other characteristic properties of the product of the present invention are:

| | |
|---|---|
| powder pore volume: | 0.35–0.65 cm³/g |
| urea content: | <0.3 wt. % |
| ureidomelamine content: | <0.3 wt. % |
| ammeline content: | <0.14 wt. % |
| ammelide content: | <0.015 wt. % |
| cyanuric acid content: | <0.01 wt. % |
| guanidine content: | <0.04 wt. % |

The preparation of melamine preferably starts from urea as the raw material in the form of a melt. $NH_3$ and $CO_2$ are by-products during the preparation of melamine, which proceeds according to the following reaction equation:

$$6\ CO(NH_2)_2 \rightarrow C_3N_6H_6 + 6\ NH_3 + 3\ CO_2$$

The preparation may be carried out at high pressure, preferably between 5 and 25 MPa, without the presence of a catalyst. The reaction temperature varies between 325 and 450° C. and is preferably between 350 and 425° C. The $NH_3$ and $CO_2$ by-products are usually recycled to an adjoining urea plant.

The above-mentioned object of the invention is for instance achieved in an installation suitable for the preparation of melamine from urea using a high-pressure process. An installation suitable for the present invention may comprise a scrubber unit, a reactor in conjunction with a gas/liquid separator or with a separate gas/liquid separator, optionally a post-reactor or ageing vessel and a cooling unit consisting of one or more vessels.

In an embodiment of the method, melamine is prepared from urea in an installation comprising a scrubber unit, a melamine reactor, a gas/liquid separator and a cooling unit. This involves urea melt from a urea plant being fed to a scrubber unit at a pressure of from 5 to 25 MPa, preferably from 6 to 15 MPa, and at a temperature above the melting point of urea. This scrubber unit may be provided with a cooling jacket in order to ensure additional cooling within the scrubber. The scrubber unit may also be provided with internal cooling bodies. In the scrubber unit the liquid urea comes into contact with the reaction gases from the gas/liquid separator downstream of the reactor. The reaction gases mainly consist of $CO_2$ and $NH_3$ and also contain an amount of melamine vapour. The molten urea scrubs the melamine vapour from the waste gas and entrains this melamine back to the reactor. In the scrubbing process, the waste gases are cooled from the temperature of the reactor, i.e. from 350–425° C., to 170–270° C., the urea being heated to 170–270° C. The off-gases are removed from the top of the scrubber unit and, for instance, recycled to a urea plant, where they are used as a raw material for the urea production.

The preheated urea is drawn off from the scrubber unit, together with the melamine scrubbed out, and supplied, for instance via a high-pressure pump, to the reactor which has a pressure of 5 to 25 MPa and preferably of 6 to 15 MPa. Alternatively, use may be made of gravity for the transfer of the urea melt to the melamine reactor by positioning the scrubber unit above the reactor.

In the reactor, the molten urea is heated to a temperature of 325 to 450° C., preferably of approximately 350 to 425° C., at a pressure as reported above, under which conditions the urea is converted into melamine, $CO_2$ and $NH_3$. An amount of ammonia may be metered into the reactor, for instance in the form of a liquid or hot vapour. The ammonia supplied may serve, for instance, to prevent the formation of undesirable condensation products of melamine or to promote mixing in the reactor. The amount of ammonia supplied to the reactor is 0 to 10 moles per mol urea; preferably 0 to 5 moles ammonia is used and in particular 0 to 2 moles ammonia per mol urea.

The $CO_2$ and $NH_3$ formed in the reaction as well as the additionally fed ammonia are separated from the liquid melamine in a gas/liquid separator placed downstream of the reactor. It may be advantageous to dose ammonia to this gas/liquid separator placed downstream of the reactor. The amount of ammonia is then 0.1–15 moles ammonia per mol melamine, preferably 0.3–10 moles. This has the advantage that the carbon dioxide is rapidly separated off, so that the formation of oxygen-containing by-products is inhibited. At a higher pressure in the reactor a larger amount of ammonia is to be used than at a lower reactor pressure.

The liquid melamine having a temperature between the melting point of melamine and 450° C. is withdrawn from the gas/liquid separator placed downstream of the reactor and may optionally be cooled to a temperature above the melting point of melamine before spraying. The melamine melt is transferred, optionally together with ammonia gas, to a cooling unit in which the liquid melamine melt is sprayed via a spraying device in an ammonia environment and cooled with a gaseous or evaporating medium at a pressure of 0.1–10 MPa, preferably 0.1–2 MPa, which results in the formation of a powder, which powder, optionally after further cooling, has a temperature below 50° C. As cooling medium use is preferably made of ammonia.

In order to influence the melam content in the multicrystalline melamine according to the invention, it was found that two essential determining parameters are the ammonia pressure in the reactor and the temperature in the reactor. An increase of melam content can be achieved by reducing the ammonia pressure in the reactor, within the limits as given. Conversely, the melam content will decrease when the ammonia pressure in the reactor is increased. An increase of melam content can also be achieved by increasing the reactor temperature, within the limits as given. Conversely, the melam content will decrease when the reactor temperature is decreased.

It was found that the use of multicrystalline melamine powder according to the invention results in an amino-formaldehyde resin with surprising special properties. This applies to both the properties during the resin preparation itself and the properties of the end products prepared using this resin.

The invention therefore also relates to amino-formaldehyde resins comprising multicrystalline melamine according to the present invention, having a high melam content, preferably higher than 1.5 wt. %, in particular higher than 2 wt. % and more in particular higher than 2.5 wt. %.

It was found that the resin preparation time can be shortened by 10–20% without reducing the initial pH. The resin preparation time is pH dependent and shows an optimum as regards the other properties. The resin stability, for instance, will decrease at a lower pH of the resin. A too high pH causes undesirable side reactions relating to the decomposition of formaldehyde. Example III and Comparative Experiment A demonstrate this shortening of the resin preparation time at the same pH of the resin solution.

It has further been found that the resins prepared with multicrystalline melamine according to the invention exhibited an improved storage stability relative to comparable resins prepared on the basis of standard melamine by means of a gas-phase process. Example IV and Comparative Experiment B show a doubling of the stability. In both experiments use was made of a formaldehyde/melamine (F/M) molar ratio of 1.5 and a formalin pH of 8.8.

Upon an increase in the F/M ratio the stability improves even further. In further experiments at higher F/M ratios a stability of 6 weeks was measured for a resin on the basis of multicrystalline melamine powder according to the invention, compared to 4 weeks for a resin having the same F/M ratio based on standard melamine obtained by means of a gas-phase process.

Resins prepared using multicrystalline melamine according to the invention also prove to be less sensitive to pH fluctuations during the preparation, so that any inaccuracy in the acid and base doses has less serious consequences for deviating condensation times and resin stability.

Besides melamine, the amino-formaldehyde resin may also contain 0–40 wt. % of another amino compound, such as for instance urea.

Amino-formaldehyde resins are often used in (decorative) top laminates, in glues and as moulding powder for the manufacture of scratch-resistant products such as crockery and electrical articles. For this, the amino-formaldehyde resins need excellent mechanical properties, for instance a high strength and surface hardness (abrasion resistance and scratch resistance) and a sufficiently high temperature resistance.

Top laminates are usually manufactured by impregnating a carrier, for instance paper, with an amino-formaldehyde resin in a way known to one skilled in the art. In doing this it was found that sheet products consisting of one or more layers of a carrier sheet that are impregnated with an amino-formaldehyde resin on the basis of multicrystalline melamine powder according to the invention, optionally supplemented with the customary additives, have excellent flexible properties upon curing (see Example V and Comparative Experiment C). Excellent flexible properties are usually obtained when use is made of resins with a low F/M ratio. When use was made of multicrystalline melamine according to the invention having 2 wt. % melam, an F/M ratio of 1.39 proved to be possible, resulting in a good post-formable low-pressure laminate (LPL). Post-formable means that an object can be deformed after having been formed. With other known melamines, for instance a melamine obtained by means of a gas-phase process, an F/M ratio of 1.39 is not possible at atmospheric conditions due to a lower dissolution rate. In Comparative Experiment C a resin on the basis of gas-phase melamine was chosen with which an F/M ratio of only 1.49 is possible at atmospheric conditions. It has been found that the post-formability of the laminate on the basis of multicrystalline melamine according to the invention of Example V was better by a factor of 2.

Surprisingly, it was also found that laminates that are made using resins made with multicrystalline melamine according to the invention show a higher surface gloss than laminates that are made using resins made with known melamines. This surprising result is illustrated in Example VI and comparative Experiment D.

Multicrystalline melamine powder according to the invention may also be used in adhesives and spray-dried powder of amino-formaldehyde resins, where the above-mentioned advantages also play a role.

The invention will be explained in more detail with reference to the following examples.

EXAMPLE I

Melamine melt having a temperature of 400° C. and a pressure of 15 MPa was introduced into a vessel by means of a spraying device and cooled with liquid ammonia, which was also sprayed into the vessel. The temperature in the vessel was 160° C. The ammonia pressure was 0.1 MPa. After 1 minute the product was cooled to ambient temperature and air was dosed to the vessel. The end product was a multicrystalline powder having the following properties:

specific surface area: 1.2 m$^2$/g content of oxygen-containing components: 0.12 wt. % color (APHA): 14

2.4 wt. % melam 0.23 wt. % melem ammonia concentration 50 ppm

EXAMPLE II

Melamine melt having a temperature of 402° C. and a pressure of 8.1 MPa was introduced into a vessel by means of a spraying device and cooled with liquid ammonia, which was also sprayed into the vessel. The temperature in the vessel was 146° C. The ammonia pressure was 1.4 MPa. After 1 minute the product was cooled to ambient temperature and air was dosed to the vessel. The end product was a multicrystalline powder having the following properties:

specific surface area: 1.3 m$^2$/g content of oxygen-containing components: 0.11 wt. % color (APHA): 15

3.2 wt. % melam 0.59 wt. % melem ammonia concentration <50 ppm

EXAMPLE III

A melam-containing melamine-formaldehyde solution was prepared by dissolving 1113 g of multicrystalline melamine according to the invention (melam content=2 wt. %; oxygen-containing components=0.4 wt. %; specific surface area=1.3 m$^2$/g; color=14 APHA) in 1589 g of a 30% formalin solution and 272 g water, the pH of which had been adjusted to 9.0 with 2 N NaOH, and then heating it to reflux temperature. After 87 minutes a water tolerance of 1.0 (g water/g resin) was reached. The water tolerance is the amount of water in gram that can be added at 20° C. to 1 g of resin before the resin turns turbid.

Comparative Experiment A

A melamine-formaldehyde resin solution as in Example II was prepared by dissolving 1113 g melamine (melam content 0.05 wt. %), obtained by means of a gas-phase process, in 1589 g of a 30% formalin solution and 272 g water, the pH of which had been adjusted to 9.0 with 2N NaOH, followed by heating to reflux temperature. In this case a water tolerance of 1.0 (g water/g resin) was reached after 110 minutes.

EXAMPLE IV

A melamine-formaldehyde resin solution was prepared by dissolving 157 g multicrystalline melamine according to the invention as used in Example III in 186 g of a 30% formalin solution and 82 g water, the pH of which had been adjusted to 8.8 with 10% aq. Na$_2$CO$_3$, and subsequently heating to 95° C. An optimum stability of 2 weeks was found at a water tolerance of 3.0 (g water/g resin).

Comparative Experiment B

A melamine-formaldehyde resin solution as in Example IV was prepared by dissolving 157 g melamine (melam content 0.05 wt. %), obtained by means of a gas-phase process, in 186 g of a 30% formalin solution and 82 g water, the pH of which had been adjusted to 8.8 with 10% aq. Na$_2$CO$_3$, and subsequently heating to 95° C. In this case the optimum stability was only 1 week at the same water tolerance as in Example IV.

EXAMPLE V

A melamine-formaldehyde resin solution was prepared by dissolving 522 g melamine according to the invention as used in Example III in 576 g of a 30% formalin solution and 165 g water, the pH of which had been adjusted to 9.3 with 4.3 g NaOH, and subsequently heating to reflux temperature. When the cloud point had been reached, the reaction temperature was lowered to 90° C. The cloud point is the point at which 1 drop of the resin added to a large amount of water at 20° C. no longer directly dissolves but shows turbidity. At the moment that a water tolerance of 1.3 (g water/g resin) was reached (within 10 minutes), the reaction mixture was cooled to room temperature.

With this resin, catalysed with paratoluene sulphonamide, paper was subsequently impregnated (120 g/m$^2$ decor paper). This impregnated paper was dried for 6 minutes at 100° C. Subsequently this impregnated paper was pressed for 30 seconds at a temperature of 160° C. and a pressure of 2.2 MPa to obtain a laminate. After cooling the post-formability was measured according to EN 438.2 (192° C., radius 6 mm). Of the samples tested, 89% passed the test successfully.

Comparative Experiment C

A melamine-formaldehyde resin solution as in Example V was prepared, as starting material use being made of 615 g standard melamine obtained by means of a gas-phase process, 729 g of 30% formalin and 172 g water. With this resin, too, a laminate was made as described in Example V. In this case 44% of the samples successfully passed the post-formability test according to EN 438-2 (192° C., radius 6 mm).

EXAMPLE VI

A melam-containing melamine-formaldehyde resin solution was prepared by dissolving 522 g melamine as obtained in example II, containing 3.2 wt. % melam, in 576 g of a 30% formalin solution and 165 g water, the pH of which had been adjusted to 9.3 with 4.3 g NaOH, and subsequently heating to reflux temperature. 55 Minutes after the cloud point had been reached, the reaction temperature was lowered to 90° C. The cloud point is the point at which 1 drop of the resin added to a large amount of water at 20° C. no longer directly dissolves but shows turbidity. At the moment that a water tolerance of 1.3 (g water/g resin) was reached (within 10 minutes), the reaction mixture was cooled to room temperature.

With this resin, catalysed with paratoluene sulphonamide, paper was subsequently impregnated (120 g/m$^2$ decor paper). This impregnated paper was dried for 6 minutes at 100° C. Subsequently this impregnated paper was pressed for 30 seconds at a temperature of 160° C. and a pressure of 2.2 MPa to obtain a laminate. After cooling the gloss was 83, measured according to EN-438-2 at an angle of 60°.

Comparative Experiment D

A melamine-formaldehyde resin solution as in Example VI was prepared; as starting material use being made of 615 g standard melamine obtained by means of a gas-phase process having melam content of 0.0 wt. %, 729 g of 30% formalin and 172 g water. With this resin, too, a laminate was made as described in Example VI. In this case the gloss was 65, measured according to EN-438-2 at an angle of 60°.

What is claimed is:

1. Multicrystalline melamine powder having the following properties:

specific surface area: 0.7–5 m$^2$/g content of oxygen-containing components<0.7 wt. %

APHA color less than 17 melam: higher than 1.5 wt. %.

2. Multicrystalline melamine powder according to claim 1, wherein the specific surface area is between 0.9 and 3 m$^2$/g.

3. Multicrystalline melamine powder according claim 1, wherein the color is lower than 15 APHA.

4. Multicrystalline melamine powder according to claim 1, wherein the melam concentration is higher than 2.0 wt. %.

5. Multicrystalline melamine powder according to claim 1, wherein the melam concentration is higher than 2.5 wt. %.

6. Multicrystalline melamine powder according to claim 5, wherein the content of oxygen-containing components is below 0.4 wt. %.

7. Multicrystalline melamine powder according to claim 1, wherein the Ammeline-Related Compounds (ARC) content is less than 0.15 wt. %.

8. Amino-formaldehyde resin comprising multicrystalline melamine with a melam content higher than 1.5 wt. %.

9. Multicrystalline melamine powder according to claim 4, wherein the Ammeline-Related Compounds (ARC) content is less than 0.1 wt. %.

10. Multicrystalline melamine powder according to claim 5, wherein the Ammeline-Related Compounds (ARC) content is less than 0.05 wt. %.

11. Amino-formaldehyde resin comprising multicrystalline melamine with a melam content higher than 2 wt. %.

12. Amino-formaldehyde resin comprising multicrystalline melamine with a melam content higher than 2.5 wt. %.

* * * * *